United States Patent
Tuma et al.

(10) Patent No.: US 8,734,432 B2
(45) Date of Patent: May 27, 2014

(54) INTEGRATION OF SURGICAL INSTRUMENT AND DISPLAY DEVICE FOR ASSISTING IN IMAGE-GUIDED SURGERY

(75) Inventors: Gregor Tuma, Münich (DE); Timo Neubauer, Neukeferloh (DE)

(73) Assignee: Brainlab AG, Feldkirchen (DE)

( * ) Notice: Subject to any disclaimer, the term of this patent is extended or adjusted under 35 U.S.C. 154(b) by 678 days.

(21) Appl. No.: 12/581,233

(22) Filed: Oct. 19, 2009

(65) Prior Publication Data
US 2010/0100081 A1 Apr. 22, 2010

Related U.S. Application Data

(60) Provisional application No. 61/107,849, filed on Oct. 23, 2008.

(30) Foreign Application Priority Data

Oct. 21, 2008 (EP) .................................. 08167095

(51) Int. Cl.
  *A61B 17/00* (2006.01)
  *A61B 19/00* (2006.01)

(52) U.S. Cl.
  CPC ............. *A61B 17/00* (2013.01); *A61B 19/5244* (2013.01); *A61B 2019/5265* (2013.01)
  USPC .......................................................... 606/1

(58) Field of Classification Search
  CPC .................. A61B 19/5244; A61B 2019/5265; A61B 2019/5483; A61B 2019/5255; A61B 2019/489
  See application file for complete search history.

(56) References Cited

U.S. PATENT DOCUMENTS

| | | | |
|---|---|---|---|
| 3,581,738 A * | 6/1971 | Moore | 600/184 |
| 4,539,585 A * | 9/1985 | Spackova et al. | 382/100 |
| 5,873,814 A * | 2/1999 | Adair | 600/109 |
| 5,954,648 A * | 9/1999 | Van Der Brug | 600/411 |
| 6,332,891 B1 * | 12/2001 | Himes | 606/169 |
| 7,643,862 B2 * | 1/2010 | Schoenefeld | 600/407 |

(Continued)

FOREIGN PATENT DOCUMENTS

| | | |
|---|---|---|
| FR | 2 830 743 | 4/2003 |
| FR | 2 852 226 | 9/2004 |

(Continued)

OTHER PUBLICATIONS

European Search Report relating to European Patent Application No. EP 12 155 187.3, dated May 18, 2012.

*Primary Examiner* — Gary Jackson
*Assistant Examiner* — Scott T Luan
(74) *Attorney, Agent, or Firm* — Tucker Ellis LLP

(57) ABSTRACT

The invention relates to a surgical instrument comprising a handle portion or mounting portion and a functional portion and/or tip, wherein a display device is provided on the instrument and includes or enables displays which serve to assist in image-guided and/or navigation-assisted surgery. It also relates to a method for navigating a surgical instrument, wherein its position is determined and tracked by means of a medical tracking system and the position data is processed within the framework of medical navigation by means of a medical navigation system, wherein displays for navigation assistance and/or for assisting in image-guided surgery are provided on the instrument or on an element which is positionally assigned to the instrument or fastened to the instrument.

28 Claims, 3 Drawing Sheets

(56) References Cited

U.S. PATENT DOCUMENTS

| | | |
|---|---|---|
| 2005/0020909 A1* | 1/2005 | Moctezuma de la Barrera et al. .............. 600/424 |
| 2006/0058644 A1 | 3/2006 | Hoppe et al. |
| 2007/0299334 A1 | 12/2007 | Vilsmeier |
| 2008/0009697 A1* | 1/2008 | Haider et al. ............... 600/407 |
| 2008/0195106 A1 | 8/2008 | Sidebotham et al. |
| 2009/0124891 A1* | 5/2009 | Shechter et al. .............. 600/424 |
| 2009/0196459 A1* | 8/2009 | Watt et al. .................... 382/103 |

FOREIGN PATENT DOCUMENTS

| | | |
|---|---|---|
| FR | 2 910 333 A1 | 6/2008 |
| WO | 98/32388 | 7/1998 |
| WO | 2004/112610 | 12/2004 |

\* cited by examiner

INTEGRATION OF SURGICAL INSTRUMENT AND DISPLAY DEVICE FOR ASSISTING IN IMAGE-GUIDED SURGERY

RELATED APPLICATION DATA

This application claims the priority of U.S. Provisional Application No. 61/107,849, filed on Oct. 23, 2008, which is hereby incorporated in its entirety by reference.

FIELD OF THE INVENTION

The invention relates to the integration of surgical instruments and display devices (and, in specific embodiments, also a computational unit) for assisting in image-guided surgery. In particular, it relates to a surgical instrument comprising a handle portion or mounting portion and a functional portion, and to a method for navigating a surgical instrument. In specific embodiments of the present invention, the surgical instrument is a pointing instrument—a so-called pointer.

BACKGROUND OF THE INVENTION

The functional portion mentioned is the portion with which the instrument is equipped in accordance with its task, i.e. for example a pointer tip in the case of a pointer instrument, a cutting edge in the case of a scalpel, or a fastening portion (the fastening portion is suitable for enabling the instrument to be attached elsewhere, in particular to other medical instruments, for example to a cutting block, an implant, a fraise, a saw, a drill, a chisel, a screwdriver, etc.) or a forcipate portion in the case of a pair of tweezers. It can also be or include a calibration receptacle which comprises a counter piece for an object to be aligned, for example in order to quickly register an image data set using a scanned counter piece. In everyday parlance, these functional portions are often also referred to as a "tip" of the instrument, and the term "tip" is also used here in this sense. It can thus also describe functional portions of instruments which are not physically embodied as a tip or embodied to be pointed.

Within the framework of navigation-assisted and/or image-guided surgery, the aforementioned pointers are in many cases used to register a patient, wherein a spatially tracked pointer is moved to various points and/or landmarks on the patient, in order to determine the spatial position of these points and/or landmarks in the navigation coordinate system of a treatment room. These points or landmarks are then assigned to corresponding points or landmarks provided in an image data set (CT, MRI, etc.) acquired for example before the treatment, and stored in the navigation system. On the basis of this, it is then possible to perform the navigation-assisted and/or image-guided treatment. In many cases, the instruments—i.e. including the pointer—are spatially tracked by optical tracking systems, wherein markings (tracking markers) attached to the instruments are tracked by cameras.

This sequence of registration steps is rather painstaking to complete using tracked pointer instruments in accordance with the prior art and conventional navigation systems, because the person performing the treatment has to constantly change their angle of view. In order to see which step follows as the next step in the registration procedure, it is necessary to look at the navigation monitor, while in parallel with this, the landmark on the patient is sought. In order to ensure that the landmark has been acquired, the surgeon again has to look at the monitor or wait for a confirmation signal. If a number of points or a point cloud (when acquiring surfaces) have to be scanned, the situation becomes even more difficult because the correct position of the pointer has to be verified again and again with the aid of the monitor—which is usually far away from the working environment.

SUMMARY OF THE INVENTION

It is an object of the present invention to facilitate the handling of a surgical instrument in the navigation environment, and in particular to make the surgeon's interaction with the instrument in the navigation environment simpler. This also applies specifically to registration tasks.

This object is solved in accordance with the invention by a surgical instrument comprising a handle portion or mounting portion and a functional portion and/or tip, wherein a display device is provided on the instrument and includes or enables displays which serve to assist in image-guided and/or navigation-assisted surgery, and by a method for navigating a surgical instrument, wherein its position is determined and tracked by means of a medical tracking system and the position data is processed within the framework of medical navigation by means of a medical navigation system, wherein displays for navigation assistance and/or for assisting in image-guided surgery are provided on the instrument or on an element which is positionally assigned to the instrument or fastened to the instrument. The sub-claims define preferred embodiments of the invention.

The surgical instrument in accordance with the present invention, which comprises a handle portion or mounting portion and a tip, has a display device provided on it which includes or enables displays which serve to assist in image-guided and/or navigation-assisted surgery, i.e. in other words, the instrument itself displays information to the surgeon which he needs during the course of the treatment, such that the surgeon does not have to look away from the instrument and/or patient in order to be able to work with navigational assistance, wherein a registration method is for example assisted in such a way that the work can proceed far more intuitively during the landmark acquisition sequence. Pointers or pointing apparatuses which are embodied in accordance with the invention can not only positionally acquire landmarks or points but can also provide information concerning the location of the landmark itself. The surgeon can concentrate his attention on the treatment location, i.e. on the incision environment, and is not distracted by looking towards the monitor.

The display device can exhibit many different configurations within the framework of the present invention. On the one hand, it can include one or more indicators which can be highlighted, in particular symbols or characters which can be illuminated or back-lit. On the other hand, it can for example comprise an image display, in particular a screen display, which can be embodied in many different forms, wherein high-resolution color monitors or also energy-saving LCD image displays are possible. In very general terms, it may be said that what is important within the framework of the invention is for the display to provide information to the physician who would otherwise have to look at the monitor. This can also include illuminated displays which are formed as points or strips and for example communicate load cases using red-amber-green displays.

In one embodiment in accordance with the invention, the position of the surgical instrument can be determined and tracked by means of a medical tracking system, wherein the position data is processed within the framework of medical navigation by means of a medical navigation system. One particular embodiment of such a tracking system (in addition to optical and magnetic tracking systems) is an integrated sensor system, specifically an inertial sensor system, which provides tracking information.

In one embodiment variant of the invention, a data processor is integrated in the instrument and assigned to the display device, wherein the activity of the instrument is tracked and identified by means of the data processor, i.e. in other words, it is also perfectly possible to evaluate the navigation and tracking data in the instrument, wherein said navigation and tracking data can in turn be provided to the surgeon via the display device.

The display device can be provided integrally with the instrument or can be able to be integrated into the instrument and/or attached to the instrument, specifically via an adaptor.

Instruments in accordance with the present invention can be provided with tracking markings; these tracking markings can in particular also be attached in the region of the display device or attached to the display device. This includes the scenario in which reflection markers or infrared LEDs are rigidly fastened to the instrument, for example two or three tracking markers in a fixed geometric (characteristic) arrangement with respect to each other.

Providing such marker arrays and/or reference arrays is however elaborate and requires calibration steps. Tracking on the basis of the shape of an object alone is in turn not robust enough against distortions in the images, background or contrast, etc.

The present invention then ensures that this is remedied, using an embodiment of the surgical instrument in which the display itself displays tracking markings or itself represents tracking markings or a tracking marking. In other words, a surgical instrument or tracking reference (for example a bone tracker) is provided in accordance with this embodiment of the invention, which can be automatically tracked or the display contents of which are tracked. This removes the need to attach tracking markings, but the tracking will nonetheless still be robust enough in order to positionally track the instrument continuously and reliably using the display device, since the display can easily be made bright enough to ensure that it is detected by the camera system. It can also be made clear enough by being colored, shaped or patterned. If, for example, the dimensions of the rectangular screen are known in the navigation system, it is possible to determine the alignment and position from the distortion in the angle of view in relation to a point of interest on the instrument or in relation to the anatomical structure. It may also be possible to directly match the display information, since it can be clearly described. The unit in which the tracking markings are displayed on the display device will also be capable of automatically or manually changing the tracking pattern, in order to adapt to particular tracking situations or to assign different instruments to different specific tracking patterns which can then be tracked in parallel.

In one embodiment in accordance with the invention, the display device includes the navigation image display. This embodiment in accordance with the invention enables the physician to perform the entire navigation with image assistance, without once having to look away from the working environment in which the instrument is situated.

It is possible to also provide the data processor of the navigation system integrally with the instrument or to enable it to be integrated into the instrument and/or attached to the instrument, specifically via an adaptor. The physician would then have a portable navigation system comprising a display and a data processor on his instrument; providing the other navigation components would be limited to providing the camera tracking system or an equivalent tracking system (magnetic tracking, etc.) and/or would even be completely omitted, i.e. if the navigation system is an inertial system which operates using acceleration, inertia and/or angle sensors integrated in the instrument, i.e. in such cases, the integrated data processor can assume the function of evaluating an inertial sensor system in the instrument, in particular also in connection with external and additional or redundant tracking information (for example, Kalman filtering), in order to improve 3D localization.

One embodiment of an instrument in accordance with the invention is characterized in that the data processor and the display device are provided as an integrated, specifically portable navigation system. This integrated system, in particular the integrated navigation system, can be able to be removably attached to the handle portion or mounting portion of the instrument via an adaptor. If the display device is directly tracked, the tracker is for example on the display and the adaptor has no tracker; if it is tracked for example via marker spheres, these are either on the display device or on the adaptor. Adapting is preferably performed in a known spatial assignment of the instrument and the adaptor with respect to each other and can be reproducibly released and reconnected.

The instrument can have a functional instrument tip as its tip (for example, a pointer instrument); it is however also possible to provide a fastening portion, for fixing the instrument, as the tip, such that the instrument itself then becomes a tracker (a tracking marking/reference) which can for example be fastened to a bone.

The method in accordance with the invention serves to navigate a surgical instrument, in particular an instrument such as has been described above in various embodiments. The position of the instrument is determined and tracked by means of a medical tracking system and the position data is processed within the framework of medical navigation by means of a medical navigation system, wherein displays for navigation assistance and/or for assisting in image-guided surgery are provided on the instrument or on an element which is positionally assigned to the instrument or fastened to the instrument.

When landmarks or surfaces are acquired and registered using the instrument, which serves as a position indicator and/or pointer, the display device can predetermine and assist in the selection of the landmarks and/or surfaces. This also applies in principle to the sequence of acquisition.

It is in principle possible to control the display device using the data processor which determines movements or point acquisitions with the aid of the navigation system or using sensors on the instrument. It is also possible to determine movements or point acquisitions with the aid of a defined movement of the trackers with respect to each other.

The visual navigation assistance can be output via a display device which is formed as a screen, and the display device can display changing tracking markings, as already described above. It is also possible within the framework of invention for the visual navigation assistance via the display device to simultaneously show the tracking markings.

The instrument in accordance with the invention can be configured such that the display device—or a navigation system which is integrated in the instrument and can include the display device—is provided as a separate element which can be attached to the instrument and comprises a sterile covering, in particular a sterile drape or a shell which is sterile and/or can be sterilized. It is also conceivable for the handle portion or mounting portion and/or the functional portion and in particular also components of the instrument which are attached to them to be formed as sterile disposable items, in particular as sterilely packaged disposable items, specifically made of a plastic material.

The embodiments of the method in accordance with the invention exhibit at least all the advantages which have already been described above with regard to the implementations of the invention as a device.

BRIEF DESCRIPTION OF THE DRAWINGS

The invention is explained below in more detail on the basis of the enclosed drawings and by referring to various embodiments. It can include any of the features described here, individually and in any expedient combination, which can represent a method, a device or a use.

DETAILED DESCRIPTION

Figure 1:
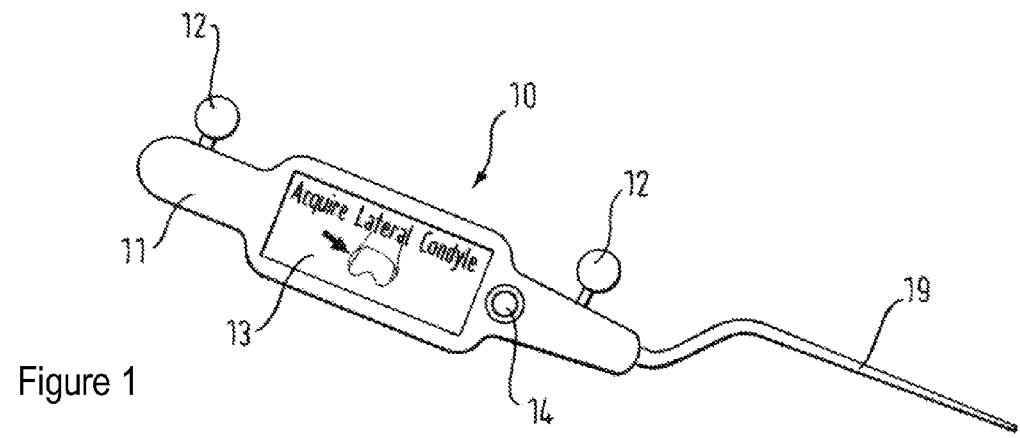
FIGS. 1 to 3 show pointer instruments embodied in accordance with the invention, comprising different display devices.
Figure 2:
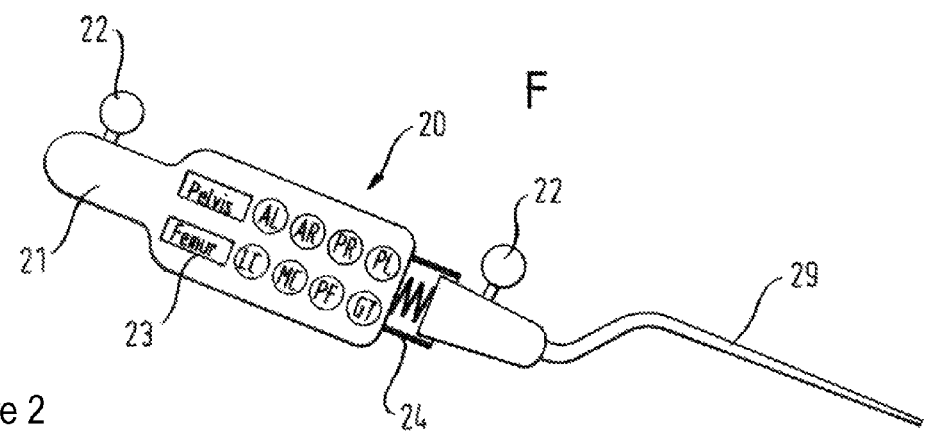
Figure 3:
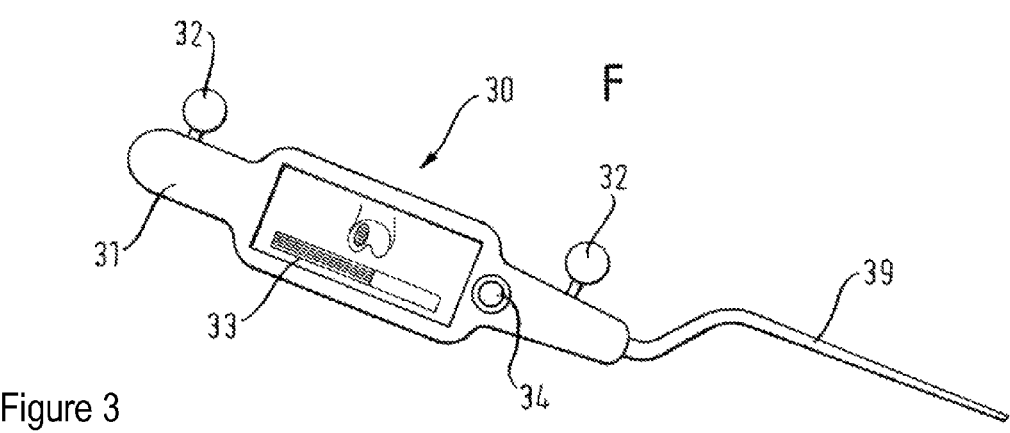

In FIGS. 1 to 7, the surgical instruments have been provided in very general terms with the reference signs 10, 20, 30, 40, 50, 60 and 70, respectively. The handles of the instruments 10, 20 and 30 bear the reference signs 11, 21 and 31, while the mounting portions of the instruments 40, 50, 60 and 70 have the reference signs 41, 51, 61 and 71, respectively. The latter mounting portions 41, 51, 61 and 71 are provided as adaptor mountings for display units and/or data processing units, in particular portable navigation systems 45, 55, 65, 75; they can, however, also be fixed mountings. Throughout the figures, the displays bear the reference signs 13, 23, 33, 43, 53, 63 and 73, respectively, and markers and/or tracking markings are indicated by 12, 22, 32, 42, 52, 62 and 72, respectively. In FIGS. 1 and 3, the reference signs 14 and 34 indicate buttons on the instrument which influence the display or enable inputs on the instrument which can also be relayed to an external navigation system.

In FIG. 2, the reference sign 24 indicates a sprung mounting of the instrument tip 29. The spring presents the possibility of automatically recording a point which is made known to the tracking system by shifting marker spheres with respect to each other in a defined way or by a force sensor system.

Figure 4:
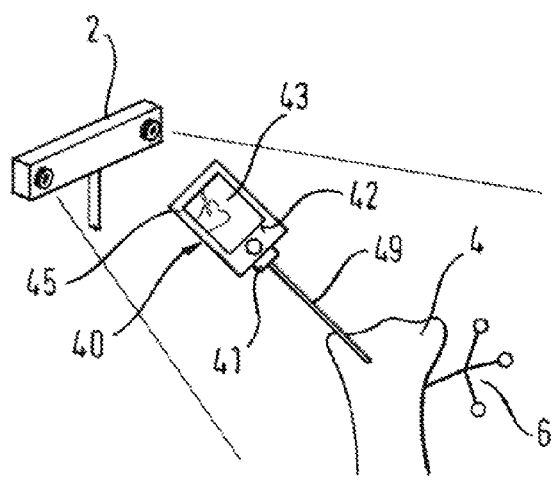
FIGS. 4 and 5 show pointers in accordance with the invention, comprising a navigation screen which also serves as a tracking reference.
Figure 5:
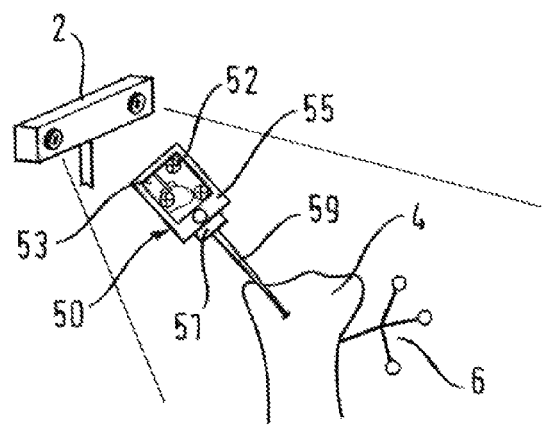
Figure 6:
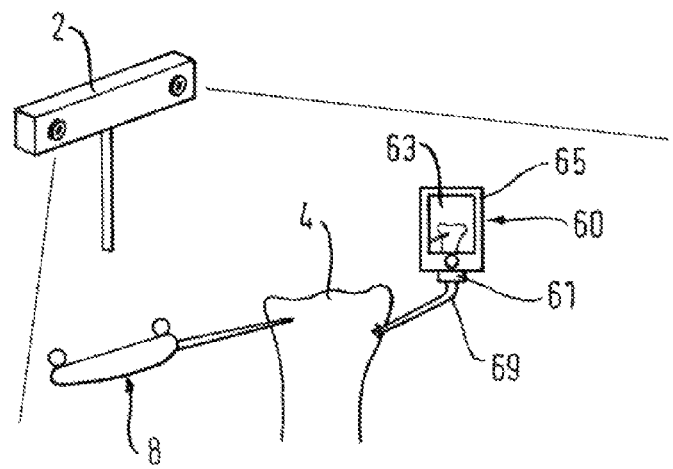
FIG. 6 shows an embodiment of the invention as a bone tracker.

The instrument tips 19, 29, 39, 49 and 59 are embodied as pointer tips in FIGS. 1 to 5, while FIG. 6 shows an instrument tip 69 which comprises a fastening means at its distal end. The reference signs 12, 22 and 32 in FIGS. 1 to 3 indicate spherical reference markers, the reference sign 42 in FIG. 4 indicates the exterior outline of the image display 43, and the reference sign 52 in FIG. 5 indicates reference markers which are generated on the image display 53. A tracking camera 2, comprising two individual cameras, and a bone 4 are also shown in each of FIGS. 4, 5 and 6; a reference array 6 comprising reference markers for the bone (bone trackers) is also shown in FIGS. 4 and 5, and FIG. 6 also shows an additional pointer instrument 8.

In the following, reference shall initially be made to FIGS. 1 to 3, in each of which a display 13, 23, 33 is provided which communicates instructions to the physician as to where a point on the patient's anatomy is to be acquired in a registration procedure. This could be achieved either by graphic representations or text (FIG. 1) or in conjunction with a display which shows whether the landmark still has to be acquired or has already been acquired. The latter applies for example to the back-lit button displays in FIG. 2, in which for example a button which is back-lit in red indicates that a certain landmark still has to be acquired and a button which is back-lit in green means that the landmark has already been acquired. The display can also give instructions—as in FIG. 3—as to how many points have already been acquired or the proportion of the total points which have already been acquired so far (bar display). This tells the user where and how many points and/or point clouds still have to be traveled using the pointer tip, in order for example to register a bone surface, i.e. in particular for morphing or surface matching using an image data set.

The pointer instruments shown in FIGS. 1 to 3 use reflective tracking markers 12, 22, 32 which can be detected by a tracking system (for example, an infrared camera system). It is possible to use other tracking technologies, for example tracking active LED markers, electromagnetic tracking or acoustic tracking.

The pointer instruments in accordance with the present invention can not only comprise displays but can also be equipped with a data processing unit which is software-controlled and can detect the acquisition of a point or point cloud autonomously and/or with the aid of the navigation system. Inertia-acceleration sensors could for example detect the current algorithmic integration of a pivoting movement of the pointer in order to acquire the point, and consequently switch the representation on the display forwards from one registration screen to the next. The discrete displays of the embodiment according to FIG. 2 could be controlled in a similar way. In this case, further communication with the navigation system is no longer necessary, but can optionally be provided and realized by the buttons 14, 34. Another way of realizing this would be to shorten the distance between the two marker spheres 22 in the embodiment according to FIG. 2 if a point is indicated by the tip 29, wherein the tip is sprung towards the handle (sprung-mounted 24).

FIGS. 4 to 6 each show how a navigation system is provided which consists of a data processing unit and display unit 45, 55, 65 and an externally provided tracking camera 2. It is conceivable for an external tracking system to be (partially) omitted if the data and display unit is equipped with an inertial sensor system, wherein the units 45, 55 and 65 can be discrete, separate and completely integrated navigation units and/or display units. They are fastened to the instrument via adaptor mountings 41, 51 and 61. In the case of FIGS. 4 and 5, the instrument has a pointer tip 49, 59; in the case of FIG. 6, the tip 69 mounts the instrument on the bone 4. Navigation information or user instructions are displayed by the navigation units 45, 55 and 65, and this could be achieved either by graphic representations or text information. In order that the instruments can be positionally tracked in space using the optical tracking system 2, the outline 42 of the screen and/or display 43 and its three-dimensional alignment are detected by the camera system 2 in the embodiment according to FIG. 4.

Alternatively, the tracking markers 52 are shown directly on the display 53 in the embodiment in accordance with FIG. 5, i.e. it is possible to generate specific patterns which generate "virtual markers". The display itself can be a pattern, since the display is defined at least in partial aspects by the programming of the graphic user interface. The increase in robustness by using known graphic representations can also mean that normal cameras (instead of infrared cameras) can be used. These solutions in accordance with the invention allow the information display to be combined with the tracker units within the line of sight to the tracking system 2. It is no longer necessary to additionally attach tracking markers.

While the two instruments 40, 50 in FIGS. 4 and 5 can serve as pointer instruments for registering landmarks, wherein the patient's anatomy is also separately tracked (the bone 4 comprising the tracking reference 6), the tracking system itself can be fastened to the instrument and via the instrument to the bone 4 in accordance with the embodiment according to FIG. 6. This enables the bone 4 to be tracked via the instrument 60 itself, using the rectangle of the display (see FIG. 4) or via superimposed markers (see FIG. 5). The instrument 60 comprising the navigation and display system 65 thus serves both as a tracking reference and as a display for the surgeon, and an additional pointer instrument 8 can be simultaneously tracked.

In all cases, the surgeon performing the treatment can obtain all the navigation information without constantly having to look away from the working environment, to look at a separate navigation monitor.

Figure 7:
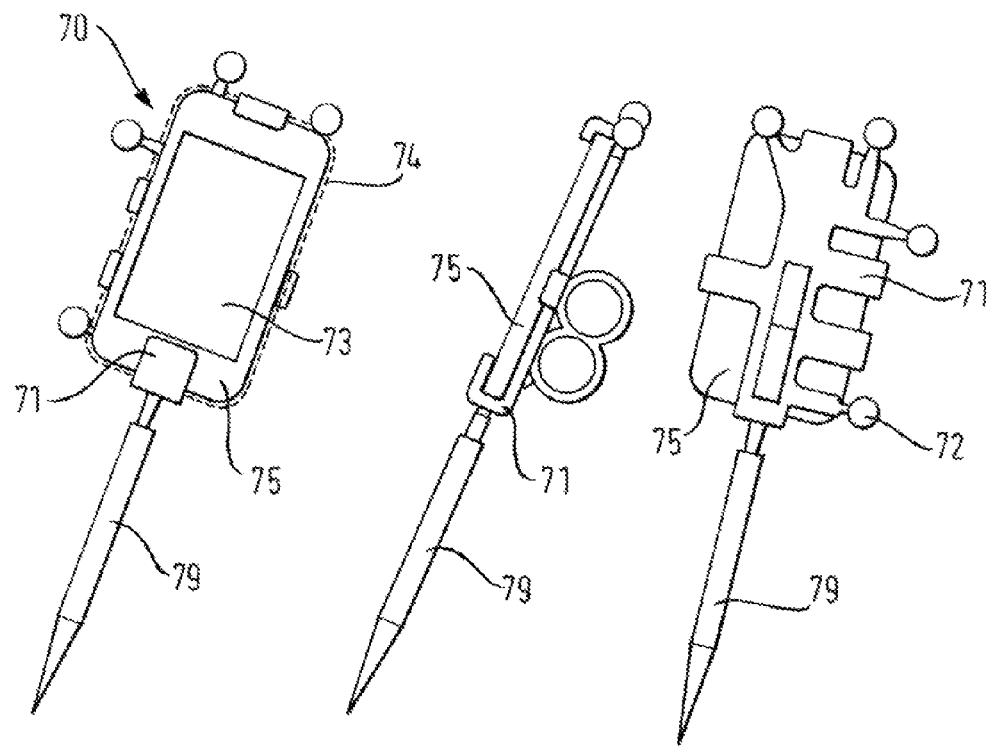
FIG. 7 shows an instrument in accordance with the invention, as a portable navigation system comprising a disposable mounting (sterile solution).
Figure 8:
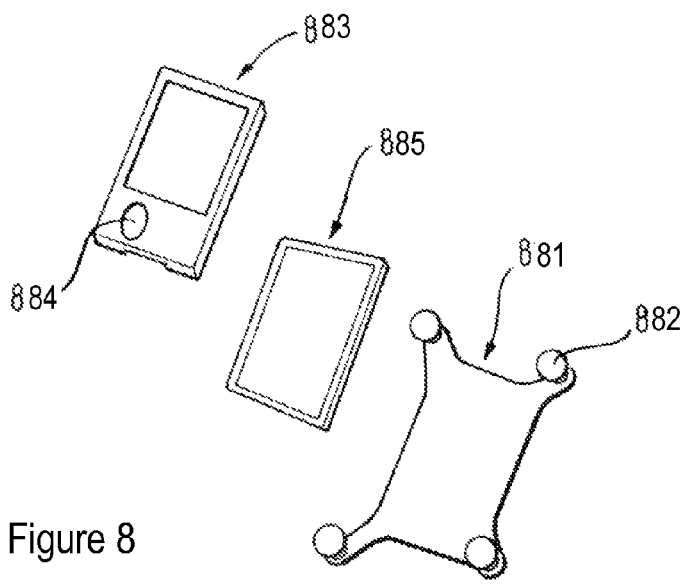
FIG. 8 shows another embodiment of a sterilely packaged, portable navigation system.

FIGS. 7 and 8 illustrate "sterile solutions" in accordance with the invention, i.e. embodiments in which an instrument in accordance with the invention comprising a display or a portable navigation system attached to the display can be sterilely used in a simple and uncomplicated way, with the aid of disposable components for handle portions or mounting portions and/or for functional portions (tip).

Using such embodiments in accordance with the invention, it is possible to use a combination of a navigation system 75 (comprising a display 73), 85 and a surgical instrument 70 in a sterile environment, wherein in the embodiment according to FIG. 7, the holding means 71 and/or the tip 79 are (individually or both) formed as disposable items (which can be used once), which can themselves also bear navigation reference markers 72. This part of the instrument would simply be provided, already sterilely packaged, in the operation environment and can be disposed of after it has been used once. It can consist substantially or completely of plastic. The mounting portion 71 forms a framework into which the portable navigation system 75 can be inserted; it also includes reference markers 72, and all manner of instrument tips can be attached to it (a pointer tip 79 is shown in this case). It can however also be an L-shaped device attached to the mounting portion 71 (for registering the distal joint line and the posterior joint line) or a cutting block.

In the embodiment according to FIG. 7, the portable navigation system 75 comprising the display 73 has been wrapped in a sterile drape (covering of film) before being inserted into the mounting 71; this drape is indicated by a broken line and has been given the reference sign 74. In this way, the navigation system 75 (comprising the display 73) is thus likewise sterilely provided and can be directly used together with the other sterile elements of the instrument. The instrument as a whole is embodied such that the user can easily interact with the navigation system or the display (for example, a touch-sensitive screen 73), while it is held in the hand and used as a surgical instrument.

As shown in FIG. 8, the holding means can also comprise a holding plate 81 comprising navigation markers 82, on which a navigation system (comprising a display 85) is placed and which is covered with a sterile, rigid covering (for example, a cover made of a transparent plastic material). The navigation system can then for example be operated via thinner points or areas of the covering 84 (also possible in the region of the screen) which it is possible to press through.

All the parts of the instrument in accordance with FIG. 7 or FIG. 8, produced in this way, can as a whole be provided as disposable parts in accordance with the invention, including the mounting portion, the instrument tip and the reference markings, such that the instrument no longer requires a sterilizing effort. This specifically applies when the sterile cover 83, 74 is also provided as a disposable item.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:
1. A surgical instrument, comprising:
a handle portion or a mounting portion;
a functional portion;
a display device configured to display information to assist in at least one of image-guided or navigation-assisted surgery, the display device comprising an image display; and a data processor assigned to the display device, wherein the data processor is configured to track and identify activity of the surgical instrument, and wherein the display device and the data processor are arranged in a common housing that is detachably connected to the surgical instrument via an adapter, wherein detachment of the housing from the surgical instrument detaches the display device and the data processor from the surgical instrument, wherein the display comprises or displays tracking markings that are trackable by a tracking system.

2. The instrument according to claim 1, wherein the display device includes at least one highlightable indicator.

3. The instrument according to claim 2, wherein the at least one highlightable indicator is configured to illuminate or back-light symbols or characters.

4. The instrument according to claim 1, wherein the image display is a screen display.

5. The instrument according to claim 1, further comprising an integrated sensor system configured to provide tracking information, said tracking information processed by a medical navigation system.

6. The instrument according to claim 5, wherein the integrated sensor system is an inertial sensor system.

7. The instrument according to claim 1, wherein the integrated data processor in the instrument is configured to evaluate an inertial sensor system in connection with external and additional or redundant tracking information in order to improve 3D localization.

8. The instrument according to claim 7, wherein the external, additional or redundant tracking information includes information obtained via Kalman filtering.

9. The instrument according to claim 1, wherein the display device includes a navigation image display.

10. The instrument according to claim 1, wherein the data processor and the display device form an integrated navigation system.

11. The instrument according to claim 10, wherein the integrated navigation system is a portable navigation system.

12. The instrument according to claim 10, wherein the integrated navigation system is removably attached to the handle portion or mounting portion via an adaptor.

13. The instrument according to claim 1, wherein the functional portion comprises at least one of
- a functional instrument tip including a fastening device configured to fixedly attach the instrument to an object, or
- a calibration receptacle configured to receive an object to be aligned to the instrument.

14. The instrument according to claim 1, wherein at least one of the display device or the data processor comprises a sterile covering.

15. The instrument according to claim 14, wherein the sterile covering is a sterile drape or a shell which is sterile.

16. The instrument according to claim 1, wherein at least one of the handle portion, the mounting portion or the functional portion is formed as sterile disposable items.

17. The instrument according to claim 16, wherein the sterile disposable items are sterilely packaged disposable items.

18. The instrument according to claim 17, wherein the sterilely packaged disposable items are made of a plastic material.

19. The instrument according to claim 16, wherein components of the instrument which are attached to the handle portion or mounting portion or the functional portion are formed as sterile disposable items.

20. The instrument according to claim 19, wherein the sterile disposable items are sterilely packaged disposable items.

21. The instrument according to claim 20, wherein the sterilely packaged disposable items are made of a plastic material.

22. A method for navigating a surgical instrument, comprising:
- providing a display device and a data processor assigned to the display device, the display device and the data processor arranged in a common housing that is detachably connected to the surgical instrument, wherein detachment of the housing from the surgical instrument detaches the display device and the data processor from the surgical instrument;
- displaying information on the display device of the surgical instrument to assist in at least one of image-guided or navigation-assisted surgery;
- using the data processor to track and identify activity of the surgical instrument,
- wherein assisting in at least one of image-guided or navigation-assisted surgery includes simultaneously displaying tracking markings via the display device.

23. The method according to claim 22, wherein the surgical instrument is an instrument according to claim 1.

24. The method according to claim 22, further comprising using the surgical instrument to acquire and register landmarks or surfaces of an object, said surgical instrument serving as a position indicator, wherein the display device predetermines or assists in the selection of the landmarks or surfaces.

25. The method according to claim 22, further comprising controlling the display device using the data processor, said data processor configured to determine movements or point acquisitions with the aid of a navigation system or using sensors on the instrument.

26. The method according to claim 22, further comprising controlling the display device using the data processor, said data processor configured to determine movements or point acquisitions with the aid of a defined movement of trackers with respect to each other.

27. The method according to claim 22, wherein assisting in at least one of image-guided or navigation-assisted surgery includes outputting information via the display device.

28. The method according to claim 22, further comprising displaying on the display device changing tracking markings.

* * * * *